United States Patent [19]

Sassano

[11] Patent Number: 4,747,826
[45] Date of Patent: May 31, 1988

[54] RAPID VENOUS INFUSION SYSTEM

[75] Inventor: John J. Sassano, Pittsburgh, Pa.

[73] Assignee: University of Pittsburgh, Pittsburgh, Pa.

[21] Appl. No.: 817,758

[22] Filed: Jan. 6, 1986

Related U.S. Application Data

[63] Continuation of Ser. No. 502,309, Jun. 8, 1983, abandoned.

[51] Int. Cl.$^4$ .............................................. A61M 31/00
[52] U.S. Cl. ...................................... 604/52; 604/113; 604/118; 604/123; 604/151; 128/DIG. 12
[58] Field of Search ................ 128/DIG. 3, DIG. 12, 128/DIG. 13, 399, 400; 604/417, 51–53, 67, 113, 114, 118, 122, 123, 151–153, 185; 422/44, 46

[56] References Cited

U.S. PATENT DOCUMENTS

| | | | |
|---|---|---|---|
| 2,642,867 | 6/1953 | Livingston | 604/245 |
| 2,835,252 | 5/1958 | Mauchel | 604/245 |
| 3,017,885 | 1/1962 | Robicsek | 128/DIG. 3 |
| 3,713,341 | 1/1973 | Madsen et al. | 128/675 |
| 3,731,679 | 5/1973 | Wilhelmson et al. | 604/121 |
| 3,827,562 | 8/1974 | Esmond | 604/122 |
| 3,896,733 | 7/1975 | Rosenberg | 604/4 |
| 3,927,980 | 12/1975 | Leonard | 128/DIG. 3 |
| 3,990,444 | 11/1976 | Vial | 604/123 |
| 4,210,138 | 7/1980 | Jess et al. | 604/123 |
| 4,228,125 | 10/1980 | Lobdell et al. | 128/DIG. 3 |
| 4,301,797 | 11/1981 | Pollack | 604/4 |
| 4,401,431 | 8/1983 | Arp | 128/DIG. 3 |
| 4,416,280 | 11/1983 | Carpenter et al. | 604/4 |
| 4,466,804 | 8/1984 | Hino | 604/4 |
| 4,490,331 | 12/1984 | Steg, Jr. | 128/DIG. 3 |
| 4,531,941 | 7/1985 | Zasuwa | 128/400 |
| 4,613,327 | 9/1986 | Tegrarian et al. | 128/DIG. 12 |

*Primary Examiner*—C. Fred Rosenbaum
*Assistant Examiner*—Mario Costantino
*Attorney, Agent, or Firm*—Reed Smith Shaw & McClay

[57] ABSTRACT

The subject invention relates to a novel system for rapid, venous infusion of a physiologic fluid, such as blood, into a patient, comprising in combination a reservoir for the physiologic fluid having an inlet port for receiving the physiologic fluid and an outlet port for dispensing the physiologic fluid, an infusion pump to propel the physiologic fluid through the system, a heating/cooling unit to control the temperature of the physiologic fluid, a sensor to monitor the pressure of the physiologic fluid, one or move cannula for infusing the physiologic fluid into the venous system of the patient, and flexible conduits connecting the components of the system to the physiologic fluid to and from each of the components of the system.

7 Claims, 1 Drawing Sheet

RAPID VENOUS INFUSION SYSTEM

This is a continuation of co-pending application Ser. No. 06/502,309 filed on June 8, 1983, now abandoned.

FIELD OF THE INVENTION

The present invention relates to fluid infusion systems in general, and to a rapid, venous infusion system specifically.

BACKGROUND OF THE INVENTION

Anesthesiologists are now regularly involved with cardiopulmonary resuscitation, trauma and organ transplantation procedures, and with maintenance of patient bodily functions during trauma and organ transplantation operations. During trauma and organ transplantation operations, patient blood loss cannot, practically speaking, be contained by the operating surgeon and must be replaced by the anesthesiologists standing in attendance. In fact, it is not uncommon for four to five anesthesiologists to stand in attendance during transplant operations lasting more than twenty-four hours attempting to infuse massive quantities of blood through five or six venous catheters pumping blood using equipment such as intravenous drip bags, piston syringes and high pressure infusion bags.

Clinical records obtained from actual operations involving trauma and liver transplantations reveal blood losses estimated to be in excess of two hundred and fifty liters, a volume approximately fifty times a normal adult's total blood volume. Although it is not uncommon for an anesthesiologist or trauma surgeon to encounter massive exsanguination (ten liters and more) in a major trauma and transplantation center, it is, however, unusual to successfully resuscitate a patient with such massive blood volume loss with traditional infusion methods.

As summarized in the table below, traditional methods of physiologic fluid administration have inherent limitations as to fluid flow rate which in turn require multiple anesthesiologists to stand in attendance to deliver a desired fluid flow rate to the patient. The data there presented represents experimental results obtained in March, 1983 at The University of Pittsburgh School of Medicine, Department of Anesthesiology Laboratory. All physiologic fluid was delivered through a ten gage catheter. The fluid consisted of a mixture of packed red blood cells, fresh frozen plasma and normal saline. The mixtures were all passed through conventional blood warmers and blood filters in the first three methods of administration and through the rapid venous infusion device of the invention in the fourth, which has its own blood filter and blood warmer.

| Method of Administration | Peak Line Pressure (mmHg.) | Fluid Flow (cc/min) | Anesthesiologists And/or Intravenous Systems Needed to Deliver 1500 cc/min |
| --- | --- | --- | --- |
| Intravenous drip | 5 | 20 | 75 |
| 50 cc piston syringe | 500 | 130 | 11.5 |
| High Pressure Infusion Bag (blood pressure cuff) | 10 | 130 | 11.5 |
| Rapid Infusion System of the Invention | 300 | 1500 | 1 |

Although apparatus and components for fluid infusion are described in the prior art, e.g., U.S. Pat. Nos. 3,731,679; 3,990,444; 4,138,288; 4,178,927; 4,210,138; 4,217,993; and 4,256,437 no system now exists which permits high volumes of a physiologic fluid, such as blood, to be successfully infused into the venous system of a patient.

A rapid, venous infusion system has now been invented which permits high volumes of physiologic fluids, such as blood, to be successfully infused. Routine fluid volumes in excess of 100 liters, and even in excess of 250 liters, have been infused with the system during trauma and transplantation operations without the mental stress and physical exhaustion encountered with traditional fluid administration methods and may even be administered by a single anesthesiologist.

SUMMARY OF THE INVENTION

The subject invention pertains to a novel system for rapid, venous infusion of a physiologic fluid, such as blood, comprising in combination a reservoir for the physiologic fluid having an inlet port for receiving the physiologic fluid and an outlet port for dispensing the physiologic fluid, an infusion pump to propel the physiologic fluid through the system, means for controlling the temperature of the physiologic fluid, means for filtering occlusive materials from the physiologic fluid, means for sensing the pressure of the physiologic fluid, means for infusing the physiologic fluid into a venous system and means for conveying the physiologic fluid to and from each of the components of the system.

In a preferred embodiment, the rapid infusion system comprises an elevated reservoir having a capacity exceeding several liters for holding a supply of physiologic fluid, preferably blood; an infusion pump selected from the group consisting of a roller head occlusive pump and a nonocclusive centrifugal pump; a heat exchanger having two chambers separated by a common wall with the physiologic fluid flowing through one chamber and a heat transfer fluid passing through the other; a micropore filter to filter any occlusive material from the physiologic fluid; an air sensor for detecting the presence of air bubbles in the physiologic fluid passing through the sensor in conjunction with means for cutting off the flow in the conduit in response to a detected air bubble along with sounding an audible alarm. Flexible conduit connects the system components including a flexible conduit connecting the reservoir to the infusion pump; a flexible conduit connecting the infusion pump with the heat exchanger; a flexible conduit leading from the heat exchanger to the filter; a flexible conduit passing from the filter to the reservoir and a flexible conduit passing from the filter through the air sensor and cut-off means terminating in at least one relatively large intravenous catheter (preferably size 8 French).

The more preferred system further includes a temperature sensor at the output of the heat exchanger for measuring the physiologic temperature and automatically adjusting the temperature and flow of the heat transfer fluid through the heat exchanger to maintain the physiologic fluid temperature within acceptable limits, and an in-line pressure sensor to monitor the pressure at a predetermined limit in order to avoid rupture of the conduits or vessels through or into which the physiological fluid is infused. The more preferred system also has readout means, such as gages, which displays fluid temperature, line pressure, fluid flow rate, and total volume of fluid infused.

DETAILED DISCRIPTION OF THE INVENTION

Figure 1:
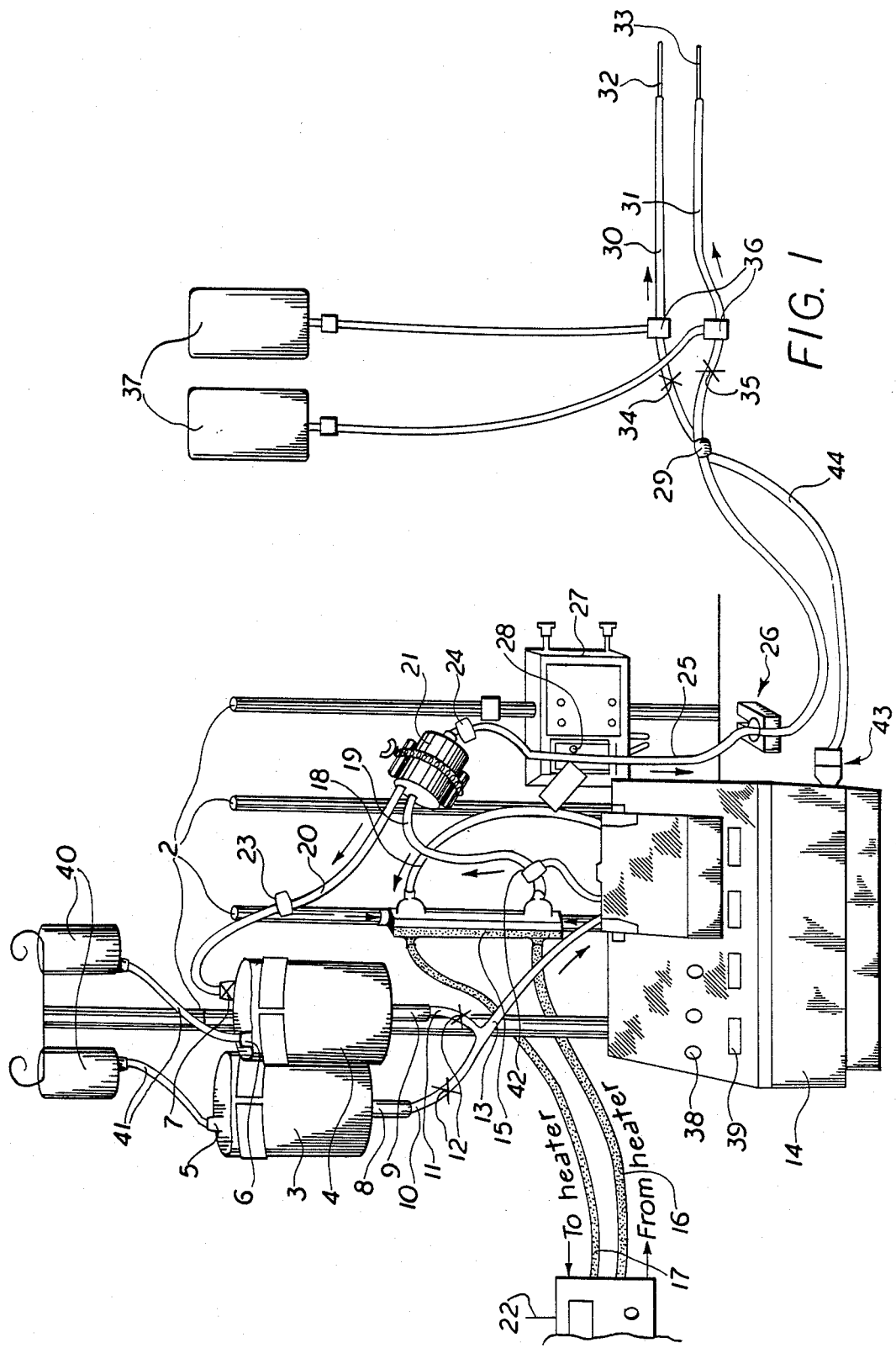
FIG. 1 is a schematic illustrating a preferred embodiment of the system according to this invention.

The rapid infusion system according to the invention may have many different embodiments. A preferred embodiment of the system is disclosed in FIG. 1 and described in detail below.

Referring now to FIG. 1, the rapid infusion system according to the invention is positioned on supporting surface 1, such as a countertop, table or the like, with individual components of the system secured to a plurality of vertical support members 2, such as standards, fixed in juxtaposition to the countertop.

Secured to one standard 2 in a position above the remaining components of the system are reservoirs 3 and 4 containing a supply of physiologic fluid, such as blood, plasma or crystalloids, preferably blood. Hang bags or bottles 40 containing blood, plasma or crystalloids may be positioned on a standard 2 above one or more of reservoirs 3 and 4 in order to fill reservoirs 3 and 4 before and during usage of the rapid infusion system. Generally such hang bags or bottles will be connected to the reservoirs through flexible conduit 41. The reservoirs 3 and 4 preferably each have a volume capacity of from about two to five liters, such volume depending on the fluid volume required during trauma or transplantation operations. The reservoirs 3 and 4 have one or more inlet ports 5 and 6 which may be adjusted to prevent a partial vaccum from forming over the surface of the physiologic fluid contained with the reservoirs. Typically, the reservoirs 3 and 4 will be disposable containers having one or more inlet ports 5 and 6 located on the top portion of each reservoir to permit the reservoirs to be refilled with the physiologic fluid.

In the depicted embodiment, reservoir 4 has three-way valve 7 positioned on the top portion of reservoir 4 to provide selective communication between reservoir 4 and the atmosphere, between reservoir 4 and return line 20 from filter 21 which filters the physiologic fluid, and positions intermediate thereto. Three-way valve 7 permits air in the physiologic fluid path to be cleared from the system and permits recirculation of the fluid to reservoir 4 to assist in mixing and regulating the temperature of the physiologic fluid contained therein.

At the bottom of each of reservoirs 3 and 4 is one or more outlet ports 8 and 9, respectively, to which flexible conduits 10 and 11 are joined by a "Y" conduit connector and terminate into pump conduit 13, also a flexible conduit. Each of conduits 8 and 9 have control means 12, such as clamps or valves, to permit selective withdrawal of the fluid from reservoirs 3 and 4.

Positioned on supporting surface 1 is infusion pump 14 through which pump conduit 13 is passed. Infusion pump 14 may be any type suitable to propel physiologic fluid through the system, such as a roller head occlusive or centrifugal pump. Such infusion pumps are known in the art as described, for instance, in U.S. Pat. Nos. 3,990,444; 4,210,138; and 4,256,437. In the rapid infusion system depicted in FIG. 1, a roller head occlusive pump manufactured by Bentley Laboratories (Model ATS-P) is used. In the operation of that pump (not shown), two rollers spaced approximately 180° apart, each mounted at the end of a shaft connected to a rotating arm, successively engage and compress pump conduit 13 against an arcuate working surface which supports pump conduit 13 to provide a pumping action. The pump has an electromagnetic stepping motor for driving the rotating arm.

In a more preferred embodiment of the rapid infusion system of the invention, adjustable control means 38 are positioned on an exterior surface of infusion pump 14 or its housing to permit control of various parameters of the physiologic fluid driven by the pump, such as fluid temperature, fluid flow rate and fluid pressure. Additionally corresponding monitoring means 39 are positioned on an exterior surface of infusion pump 14 or its housing to permit the monitoring and display of various parameters of the physiologic fluid driven by the pump, such as fluid temperature, fluid flow rate, fluid pressure and total volume of fluid administered.

Mounted on another standard 2 is a heat exchanger 15 defined by two compartments separated by a common wall. The heat exchanger 15 is designed to control the temperature of the physiologic fluid to be administered to the patient. Both the principles of heat exchangers, and suitable heat exchangers embodying these principles, are known in the prior art. In the rapid infusion system depicted in FIG. 1, a heat exchanger unit manufactured by Travenol (Model No. 5M0337) is used. Preferably, the heat exchanger is disposable. In the operation of the heat exchanger, heat transfer fluid is circulated through one compartment, while the physiologic fluid is circulated through the second compartment, preferably in the opposite flow direction.

The heat transfer fluid is conveyed to and from heat exchanger 15 by flexible conduits 16 and 17, respectively, while the physiologic fluid is conveyed to the heat exchangers from infusion pump 14 by flexible conduit 18 and from the heat exchanger by flexible conduit 19. Preferably, the flexible conduits used in the system are plastic disposable tubing. The temperature of the physiologic fluid exiting from heat exchanger 15 is monitored by sensing means 42 positioned in juxtaposition to the outlet of the compartment on flexible conduit 19 through which the physiologic fluid flows. In one embodiment, sensing means 42 may be a sterile probe placed in the fluid path via a leur-lock mechanism. Sensing means 42 in turn signals heating/cooling unit 22 to adjust the temperature of the heat transfer fluid flowing through the other compartment of the heat exchanger to control the temperature of the physiologic fluid exiting heat exchanger 15. In the rapid infusion system depicted in FIG. 1, a heating/cooling unit manufactured by Blanketrol (Model No. 73ATAX) is used.

Heating/cooling unit 22 may be an independent component of the system or integrated into rapid infusion pump unit 14. Within the operating limits of the rapid infusion system of the invention, heat exchanger 15 in combination with heating/cooling unit 22 maintains the temperature of the physiologic fluid to be administered within a desired range regardless of the flow rate of the physiologic fluid, and the possibility of damage occurring to the physiologic fluid due to temperature extremes or variations is minimized.

The physiologic fluid flows from the outlet of heat exchanger 15 to the inlet of filtering means 21 through flexible conduit 19. Filtering means 21 may be a micropore filter and filters out any microemboli and air entrained in the physiologic fluid. Such a micropore filter is preferably a sterile, pyrogen-free disposable filter which filters particles from the physiologic fluid (preferably blood) which are 40 microns and greater in size. Such particles would include platelet aggregates, fatty bodies, red blood cell agglomerates. Such filtering means and micropore filters are known in the prior art.

In the rapid infusion system depicted in FIG. 1, a micropore filtering unit manufactured by Pall (Model No. EC3840) is used. Purge line 20 connects an outlet port of filtering means 21 to an inlet port of reservoir 4 through three-way valve 7. Clamping means 23 or other suitable means for restricting flow, such as a pinch clamp, is positioned on purge line 20 to constrict purge line 20 to a closed position when administering the physiologic fluid to a patient and to maintain purge line 20 in an open position when recirculating the physiologic fluid to reservoir 4 rather than to the patient. A second clamping means 24, or other suitable means for restricting flow, such as a pinch clamp, is positioned on flexible conduit 25 leasing from an outlet port of filtering means 21 to constrict to a closed position flexible conduit 25 when recirculating the physiologic fluid to reservoir 4 to prevent physiologic fluid flowing simultaneously to the patient as well as to reservoir 4. Clamping means 24 may also partially constrict flexible conduit 25 in order to recirculate one portion of the physiologic fluid while a second portion of the physiologic fluid is administered through the system. Such partial recirculation permits further control of the volume of physiologic fluid administered by the system.

Flexible conduit 25 next transports the physiologic fluid from an outlet port of filter 21 through an air bubble detector 26 and interrelated automatic cut-off mechanism 27. Such a detector and cut-off mechanism are known in the art and are disclosed in U.S. Pat. Nos. 4,210,138 and 4,256,437. The detection of air bubbles in the physiologic fluid in flexible conduit 25 discontinues the flow of physiologic fluid in the infusion system, closes clamp 28, or other restrictive means, positioned on flexible conduit 25 and alerts the system operator by an alarm mechanism. In the rapid infusion system depicted in FIG. 1, an air bubble detector and interrelated cut-off mechanism manufactured by Renal Systems (Model No. RS3220A) is used which works on a doppler ultrasound method of detecting air or air/fluid interfaces.

In a preferred embodiment, a pressure sensor 43 is connected by connective means 29 to flexible conduit 25 to measure physiologic fluid pressure in the conduit, and the measured pressure is displayed by monitoring means 39 and regulated by adjustable control means 38 positioned on an exterior surface of infusion pump 14 or its housing. Pressure sensor 43 is preferably connected to connective means 29 by flexible conduit 44. Suitable pressure sensors are known in the art. Such pressure measurements lessen the possibility of either conduit or venous rupture occurring during use of the system.

In a most preferred embodiment, pressure sensor 43 is a sensor which permits sterile separation between monitoring means 39 and the physiologic fluid, preferably blood, being sensed, while simultaneously permitting accurate pressure sensing and transmission. In the rapid infusion system depicted in FIG. 1, a pressure sensor manufactured by Delta Medical Co. (Model No. PMS-2) having a disposable non-permeable, plastic membrane is used. Such a sensor minimizes bacterial contamination during pressure monitoring.

Generally, flexible conduit 25 is divided downstream of pressure sensor 29 by a "Y" shaped conduit connector into flexible conduits 30 and 31 which terminate in intravenous cannulae 32 and 33 of relatively large diameter, i.e., No. 10 gauge or 8 French. Control means 34 and 35 positioned on output conduits 30 and 31 permit selective delivery of the physiologic fluid through one or both output conduits.

Three-way stopcocks 36 positioned in juxtaposition to flexible conduits 30 and 31 connect conduits 30 and 31 to one or more sources 37 of supplemental or medicinal intravenous fluid which may be trickled into a patient's venous system to keep the veins patent when the physiologic fluid is not being rapidly infused into the patient.

In the most preferred embodiment of the system, the pressure sensing, temperature sensing, flow and volume sensing and air bubble sensing devices are electrical or electronic in nature, and the output signal from each sensor is directed to the appropriate component or components of the system to enable automatic system pressure temperature, flow and volume regulation with corresponding display.

Unlike standard or traditional methods of intravenous fluid administration, the rapid infusion system according to the invention and disclosed above provides total adult human blood volume (five liters) in reserve, rapidly regulates fluid temperature with minimal increase in resistance to flow, easily and rapidly administers massive quantities of blood (in clincal use over two hundred fifty liters have been administered) to a single patient during a single operation, administers physiologic fluid maintained at a predetermined temperature at flow rates in excess of one and one-half liters per minute, and permits simultaneous display and control of fluid temperature, flow rate, line pressure, and total volume of physiologic fluid administered. The system also is portable and able to be quickly and easily set up and functioning in an emergency situation (emergency room trauma or surgical hemorrhage). Surprisingly, unlike cardiopulmonary bypass systems, the system according to the invention does not require heparin or an anticoagulant to function successfully and effectively over an extended period of time.

Although the invention has been described in detail for the purposes of illustration, it is to be understood that such detail is solely for that purpose and that variations can be made therein by those skilled in the art without departing from the spirit and scope of the invention except as it it may be limited by the claims.

What is claimed is:

1. A system for venous infusion of a physiologic fluid, such as blood, into a patient at a flow rate of at least one liter per minute comprising in combination:
   a. a reservoir for the physiologic fluid having an input port for receiving the physiologic fluid and an outlet port for dispensing the physiologic fluid;
   b. a container containing physiologic fluid not obtained directly from the patient to be furnished to the reservoir;
   c. a rollerhead occlusive pump or a centrifugal pump for propelling the physiologic fluid through the system at a flow rate of at least about one liter per minute;

d. a heat exchanger with an interrelated heating-/cooling unit;

e. a micropore filter having a pore size of 40 microns or less;

f. a pressure sensor;

g. an air bubble sensor with an associated cut-off mechanism;

h. one or more intravenous cannula of a relatively large diameter;

i. flexible conduit means connecting the container to the reservoir, the reservoir to the infusion pump, the infusion pump to the heat exchanger, the heat exchanger to the micropore filter, the micropore filter to the reservoir and the micropore filter to the air bubble sensor and associated cut-off mechanism, and terminating at the intravenous cannula;

j. means in said system for sensing the temperature, flow rate and total volume of the physiologic fluid to be infused; and k. means in said system for controlling the temperature, flow rate, pressure and total volume of the physiologic fluid to be infused.

2. The system of claim 1 wherein the reservoir has a volume capacity of two to five liters.

3. A method for rapid infusion of a physiologic fluid, such as blood, into the venous system of a patient, comprising the steps of:

a. providing a reservoir of a physiologic fluid to be infused into a patient;

b. propelling the physiologic fluid from the reservoir by an infusion pump through a plurality of intervening steps into the venous system of the patient at a flow rate of at least about one liter per minute;

c. controlling the temperature of the physiologic fluid propelled by the infusion pump;

d. filtering the physiologic fluid to remove materials which could prove to be occlusive in the cardiovascular system of the patient;

e. detecting any air bubbles present in the physiologic fluid and interrupting the flow of the physiologic fluid being infused into the patient upon detection of any such air bubbles; and f. monitoring the fluid pressure of the physiologic fluid being infused into the patient to lessen the possibility of rupture in either the venous system of the patient or in the apparatus delivering the physiologic fluid to the patient.

4. A system for rapid venous infusion of a physiologic fluid such as blood into a patient a flow rate of at least about one liter per minute, consisting essentially of:

a. a reservoir for the physiologic fluid having an inlet port for receiving the physiologic fluid and an outlet port for dispensing the physiologic fluid;

b. infusion pumping means for propelling the physiologic fluid through the system at a flow rate of at least one liter per minute;

c. means for controlling the temperature of the physiologic fluid;

d. means for filtering occlusive materials from the physiologic fluid;

e. means for sensing the pressure of the physiologic fluid;

f. means for infusing the physiologic fluid into the venous system of the patient; and g. connective means for conveying physiologic fluid from the reservoir to and from each of the other components of the system to the means for infusing the physiologic fluid into the venous system of the patient.

5. The system of claim 4 further consisting essentially of means for sensing air bubbles in the physiologic fluid.

6. A system for rapid venous infusion of a physiologic fluid, such as blood, into a patient at flow rate of at least about one liter per minute, consisting essentially of:

a. a reservoir for the physiologic fluid having a volume capacity of two to five liters and having an inlet port for receiving the physiologic fluid and an outlet port for dispensing the physiologic fluid;

b. a roller head occlusive pump or centrifugal pump for propelling the physiologic fluid through the system at a flow rate of least about one liter per minute;

c. a heat exchanger with an interrelated heating/cooling unit;

d. a micropore filter having a pour size of 40 microns or less;

e. a pressure sensor;

f. an air bubble sensor with an associated cut-off mechanism;

g. one or more intravenous cannula of a relatively large diameter; and h. flexible conduit means connecting the components in combination to convey the physiologic fluid from the reservoir to and from each of the other components of the system to the cannula.

7. A system for venous infusion of a physiologic fluid, such as blood, into a patient at a flow rate of at least one liter per minute consisting essentially of:

a. a reservoir for the physiologic fluid having an input port for receiving the physiologic fluid and an outlet port for dispensing the physiologic fluid;

b. a rollerhead occlusive pump or a centrifugal pump for propelling the physiologic fluid through the system at a flow rate of at least about one liter per minute;

c. a heat exchanger with an interrelated heating/cooling unit;

d. a micropore filter having a pore size of 40 microns or less;

e. a pressure sensor;

f. an air bubble sensor with an associated cut-off mechanism;

g. one or more intravenous cannula of a relatively large diameter;

h. flexible conduit means connecting the reservoir to the infusion pump, the infusion pump to the heat exchanger, the heat exchanger to the micropore filter, the micropore filter to the reservoir and the micropore filter to the air bubble sensor and associated cut-off mechanism, and terminating at the intravenous cannula;

i. means in said system for sensing the temperature, flow rate, and total volume of the physiologic fluid to be infused; and j. means in said system for controlling the temperature, flow rate, pressure, and total volume of the physiologic fluid to be infused.

* * * * *

UNITED STATES PATENT AND TRADEMARK OFFICE
CERTIFICATE OF CORRECTION

PATENT NO. : 4,747,826

DATED : May 31, 1988

INVENTOR(S) : John J. Sassano

It is certified that error appears in the above-identified patent and that said Letters Patent is hereby corrected as shown below: Title page:

In the Abstract, five lines from the bottom, change the word "move" to -- more -- ;

At column 1, line 14, change the word "cardiopulmonany" to -- cardiopulmonary -- ;

At column 4, line 32, change the word "these" to -- those --.

At column 5, line 27, change the word "leasing to -- leading -- ;

At column 6, line 36, change the word "clincal" to -- clinical -- ;

In Claim 4, column 7, line 53, change the phrase "patient a" to -- patient at a -- ;

In Claim 6, column 8, line 23, change the word "pour" to -- pore -- .

Signed and Sealed this

Twenty-ninth Day of November, 1988

*Attest:*

DONALD J. QUIGG

*Attesting Officer*     *Commissioner of Patents and Trademarks*